United States Patent [19]

Selin et al.

[11] Patent Number: 4,976,844
[45] Date of Patent: Dec. 11, 1990

[54] SENSOR CONSTRUCTION

[76] Inventors: Lauri Selin; Pertti Aaltonen; Heikki Illi, all of VTT Metallilaboratorio, Kemistintie 3, SF-02150 Espoo, Finland

[21] Appl. No.: 424,207
[22] PCT Filed: Jan. 4, 1988
[86] PCT No.: PCT/FI88/00001
  § 371 Date: Oct. 12, 1989
  § 102(e) Date: Oct. 12, 1989
[87] PCT Pub. No.: WO88/08127
  PCT Pub. Date: Oct. 20, 1988

[30] Foreign Application Priority Data

Apr. 13, 1987 [FI] Finland .................. 871618

[51] Int. Cl.$^5$ ............................ G01N 27/30
[52] U.S. Cl. .................................. 204/408
[58] Field of Search ............... 204/408, 435, 416, 420, 204/415, 417, 418, 419

[56] References Cited

U.S. PATENT DOCUMENTS

| 2,697,070 | 12/1954 | Arthur | 204/408 |
| 3,145,158 | 8/1964 | Matsuyama | 204/435 |
| 3,445,366 | 5/1969 | Vermeer | 204/408 |
| 4,273,637 | 6/1981 | MacDonald | 204/408 |
| 4,406,766 | 9/1983 | MacDonald | 204/433 |
| 4,818,366 | 4/1989 | Yonco et al. | 204/408 |

FOREIGN PATENT DOCUMENTS

| 0076464 | 4/1983 | European Pat. Off. | 27/30 |
| 0215178 | 3/1987 | European Pat. Off. | 27/30 |
| 338184 | 8/1971 | Sweden | 27/30 |

Primary Examiner—G. L. Kaplan
Attorney, Agent, or Firm—Kane, Dalsimer, Sullivan, Kurucz, Levy, Eisele & Richard

[57] ABSTRACT

The invention relates to a sealing and insulating construction of a sensor for pressurized working conditions. The construction comprises a pressure balancing chamber (1) which is open towards the pressurized space, a sensor (4) which is partly located within the chamber and partly protrudes therefrom, as well as a conductor (6) insulated from the housing (2) and coupled to the sensor (4), and brought into the chamber via a leadthrough (5). Moreover, the construction includes insulation (7) for filling the space that surrounds the chamber around the sensor, as well as a piston (8) for separating the insulation around the sensor from the pressurized space, so that under pressure the sensor is evenly loaded on all sides, and consequently not subject to such tensions that could break it.

11 Claims, 1 Drawing Sheet

U.S. Patent     Dec. 11, 1990     4,976,844
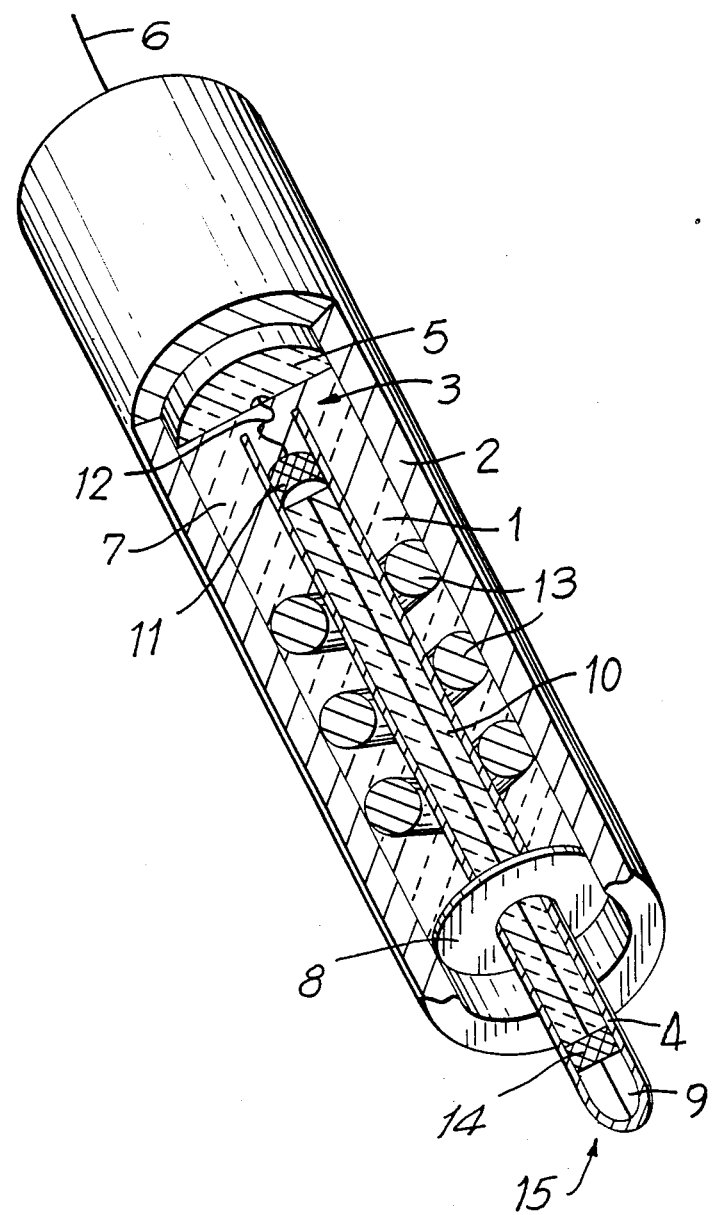

SENSOR CONSTRUCTION

The present invention relates to a sensor construction particularly for the sealing and electrical insulation of ceramic or other fragile membranes in pressurized conditions where high temperatures prevail.

While using high pressures and high temperatures, the problem is the leading through of the sensors into these spaces so that they are not damaged under the influence of the fluctuation of pressure and temperature. For example in the measurements of pH and oxygen, the common practice is to use relatively fragile sensors, which may be easily broken under pressure when brought into a pressurized space.

The object of the present invention is to eliminate the above mentioned drawbacks. A particular object of the present invention is to introduce a sensor construction which also enables the use of fragile materials in sensors under high pressures.

As regards the characteristic novel features of the invention, the claims section is referred to.

The invention is based on the principal idea that the fragile sensor is placed in a pressurized space in an essentially freely movable position, to float in the insulating material so that an equally high pressure is effective on all sides of the fragile construction.

The sensor construction of the invention comprises a housing which forms the pressure balancing chamber and is essentially open towards the pressurized space; a hollow tubular sensor, open at the end nearest to the said chamber, partly located in this chamber and partly protruding out of it, the measuring chamber of the sensor being located at the outermost, closed end of the said sensor; and a conductor, which is lead into the chamber via a leadthrough arrangement known as such, and is connected to the sensor and insulated from the housing. Moreover, the space of the chamber surrounding the sensor is mainly filled with the insulating material, which is separated from the pressurized space by means of the advantageously annular piston provided around the sensor.

The sensor is advantageously a hollow rod-like ceramic or other fragile membrane open at one end and closed at the other, and a conductor is led into its outermost closed end, i.e. to the measuring chamber, via the open end. In between the measuring chamber and the open end of the sensor, there is a sealing chamber separated by means of screw units, which sealing chamber is filled with the insulating material while the screw units are freely movable under the influence of the pressure in the lengthwise direction of the sensor.

At the innermost end of the chamber, the part of the conductor which is located in between the screw unit and the leadthrough of the conductor, is bent to form a loose curve so that the sensor can be moved with respect to the housing without obstruction by the conductor. Advantageously the part of the chamber surrounding the sensor is provided with one or several guides, for instance sliding seal rings, which are arranged to be supported both by the sensor and the inner surface of the pressure balancing chamber so that they essentially prevent any transversal movements of the sensor, but allow the sensor to move freely in the lengthwise direction.

In the vicinity of the open end of the chamber, the piston sealing the space in between the chamber and the sensor can be a separate elastic ring, which is freely movable with respect to the walls of both the sensor and the chamber. It can also be an essential part of the sensor, for example made of the same ceramic material as the sensor, in which case the outer edge of this flange, resting against the chamber, is provided with sealing which prevents the insulating material from entering the other side of the piston. An essential feature for the insulating material, the piston and the guides is that they are all non-conducting so that the sensor is galvanically insulated from the housing.

The advantage of the invention, compared with the prior art, is that it enables the use of fragile sensors in high pressures and high temperatures, which has not been possible with the current methods.

In the following the invention is explained in detail with reference to the appended drawing, where a sensor construction according to the invention is illustrated.

The preferred embodiment of the sensor construction of the invention, illustrated in the drawing, includes a straight, tubular pressure balancing chamber 1 formed by the housing 2, which chamber is open at one end and closed at the other. At the closed end of the chamber, there is located the leadthrough 5 of the insulated conductor 6, which leadthrough leads the conductor into the pressure balancing chamber in a pressure-proof manner and insulated within the housing 2. Partly inside the chamber and partly protruding therefrom, there is arranged a tubular sensor 4 made of some fragile material, which sensor is open at its inner end closed at its outer end. The closed end of the sensor comprises the measuring chamber 9, and the rest of the inside of the sensor is filled with insulating material 10 placed in between two screw units 11 and 14. The insulated conductor, led via the leadthrough into the pressure balancing chamber, is arranged to proceed through the first screw unit 11, the insulating material 10 and the second screw unit 14 into the measuring chamber. The part 12 of the conductor which remains in between the first screw unit and the leadthrough, is allowed to form a loose curve, thus enabling the sensor to move freely with respect to the housing 2.

The sensor 4 is supported against the pressure balancing chamber 1, in the vicinity of the open end of the chamber, by means of an annular, elastic piston 8, so that the inner part of the said chamber, separated by the piston, is filled with some insulating compond or liquid 7, which is for instance Teflon (polytetrafluoroethylene) or silicone. Moreover, further inside the chamber the sensor is supported against the chamber walls by the sliding seal rings B, which essentially prevent the sensor from moving transversally in the chamber, but allow it to move freely in the lengthwise direction thereof.

The sensor construction of the invention is operated as follows. While pressure is effective outside the tip 15 of the sensor 4, the piston 8 is pushed inside and presses the insulation 7 located in the pressure balancing chamber 1. The pressure enters, via the chamber-side open end 3 of the sensor, to the inside of the sensor, so that the first screw unit 11 presses the sealing material 10, and this in turn presses the second screw unit 14, thus causing the pressure in the measuring chamber 9 to be equal to the pressure in the pressurized space on the other side of the fragile ceramic. The sensor 4 itself can move freely in the lengthwise direction, supported by the piston 8 and the guides 13, because the sensor is not attached to the housing in a rigid fashion, but only flexibly by intermediation of the conductor 6. Thus the fragile sensor material is evenly loaded on all sides, so that it is not subject to tensions and can resist high pressures. Moreover, the electric insulation required in measurement-technical applications is achieved by employing the disclosed construction.

In the above specification, the invention has been explained with reference to one preferred embodiment only. It does not, however, restrict the invention in any way, but the different modifications thereof can vary within the scope of the appended patent claims.

We claim:

1. A sealing and insulating construction for a sensor, to be used in pressurized conditions, which construction comprises
    a housing (2) which is essentially open towards the pressurized space and forms the pressure balancing chamber (1);
    a tubular sensor (4) partly located within the said chamber and partly protruding therefrom;
    a conductor (6) connected to the sensor and insulated from the housing of the construction, brought into the chamber by means of a leadthrough arrangement (5);
    characterized in that the construction includes insulation (7) which for the most part fills the space of the chamber (1) surrounding the sensor (4), as well as a piston (8) placed around the sensor, which piston separates the insulation from the pressurized space, the said sensor being open at its chamber-side end and insulated from the housing so that an essentially equal pressure prevails both inside and outside the sensor.

2. The construction of claim 1, characterized in that the pressure balancing chamber (1) is a tubular space open at its one end.

3. The construction of claim 1, characterized in that the sensor (4) is a rodlike ceramic or other fragile membrane, the outer end whereof is provided with a measuring chamber (9) whereto the conductor (6) is connected.

4. The construction of claim 3, characterized in that the sensor (4) includes a sealing chamber (10) which is separated from the measuring chamber (9) and from the open end of the sensor by means of screw units (11, 14).

5. The construction of claim 3, characterized in that the part (12) of the conductor located in between the leadthrough (5) and the sensor (4) forms a loose curve in order to allow the sensor to move with respect to the housing (2).

6. The construction of claim 1, characterized in that the insulation (7) is a non-conducting insulating material.

7. The construction as claimed in claim 6 wherein said non-conducting insulating material is selected from a group consisting of poly tetrafluoroethylene and silicone.

8. The construction of claim 1, characterized in that the chamber (1) surrounding the sensor (4) comprises guides (13), in order to support the sensor so that it is freely movable with respect to the chamber.

9. The construction as claimed in claim 8, wherein said guides are sliding seal rings.

10. The construction of claim 1, characterized in that the piston (8) is an at least partly elastic flange which under pressure is urged into a compact contact against the chamber (1).

11. The construction of claim 10, characterized in that said piston (8) is an annular, elastic member which under pressure is freely movable both with respect to the chamber and to the sensor, and that the pressure urges it into a compact contact against them.

* * * * *